United States Patent
George et al.

(10) Patent No.: US 12,029,216 B1
(45) Date of Patent: Jul. 9, 2024

(54) THIOPHENE ACETIC ACID FOR PLANT GROWTH REGULATION

(71) Applicant: United Arab Emirates University, Al Ain (AE)

(72) Inventors: Suja George, Al Ain (AE); Khaled M. A. Amiri, Al Ain (AE); Mohammed Rafi, Al Ain (AE); Maitha Aldarmaki, Al Ain (AE); Mohamed ElSiddig, Al Ain (AE); Mariam Al Nuaimi, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 18/238,934

(22) Filed: Aug. 28, 2023

(51) Int. Cl.
*A01N 43/10* (2006.01)
*A01N 43/90* (2006.01)
*A01P 21/00* (2006.01)

(52) U.S. Cl.
CPC ............ *A01N 43/10* (2013.01); *A01N 43/90* (2013.01); *A01P 21/00* (2021.08)

(58) Field of Classification Search
CPC .......... A01N 43/10; A01N 43/90; A01P 21/00
See application file for complete search history.

(56) References Cited

U.S. PATENT DOCUMENTS

| | | | | |
|---|---|---|---|---|
| 9,968,088 B2 * | 5/2018 | Wikeley | | C05G 3/00 |
| 2014/0179000 A1 * | 6/2014 | Laine | | A01H 4/008 |
| | | | | 435/430 |

FOREIGN PATENT DOCUMENTS

ES    2800281 T3 *   12/2020   ........... A01H 4/005

OTHER PUBLICATIONS

ES 2800281 T3 machine translation (Year: 2020).*
Yoshihiko Inamori, Chikaaki Muro, Kyoko Osaka, Yuichiro Funakoshi, Yoshihide Usami, Hiroshi Tsujibo, and Atsushi Numata, "inhibitory Activities of 3-Thiophenecarboxylic Acid and Related Compounds on Plant Growth", Bioscience, Biotechnology, and Biochemistry, 58(7), 1336-1337, 1994. (Year: 1994).*
Yoshihiko Inamori, Chikaaki Muro, Yuichiro Funakoshi, Yoshihide Usami, Hiroshi Tsujibo, and Atsushi Numata, "Phytogrowth-Inhibitory Activities of 2-Thiophenecarboxylic Acid and Its Related Compounds", Biological and Pharmaceutical Bulletin, 17(1), 160-162, 1994. (Year: 1994).*
Borje Aberg, "Plant Growth Regulators", Swedish Journal of Agricultural Research, 13: 3-6, 1983. (Year: 1983).*

* cited by examiner

*Primary Examiner* — Mina Haghighatian
*Assistant Examiner* — Nathan W Schlientz
(74) *Attorney, Agent, or Firm* — MH2 TECHNOLOGY LAW GROUP, LLP

(57) ABSTRACT

A plant growth regulator contains thiophene acetic acid. A method of regulating growth of plants includes preparing a plant growth regulator comprising thiophene acetic acid and applying the plant growth regulator. Shoot regeneration from tomato cotyledon explants in vitro is enhanced in the presence of the antibiotic timentin. Timentin degrades into thiophene acetic acid (TAA) over time. Thiophene acetic acid (TAA) performs particularly well as a plant growth regulator. TAA was surprisingly found to enhance root and shoot formation and growth in explants, and in particular in cotyledon explants. TAA is also advantageous in that it may be used to enhance growth in whole plants.

2 Claims, 6 Drawing Sheets

| TREATMENT (basic media + compound) | ROOT REGENERATION PERCENTAGE (%) | AVERAGE NUMBER OF ROOTS PER EXPLANT |
|---|---|---|
| Basic Media | 76.67 a | 1.56 ab |
| 300 mg/L timentin | 60.00 a | 1.33 ab |
| 0.05 mg/L TAA | 70.00 a | 1.50 ab |
| 0.05 mg/L IBA | 56.67 a | 1.52 ab |
| 0.05 mg/L IAA | 50.00 ab | 1.85 ab |
| 0.05 mg/L NAA | 46.67 ab | 2.38 a |
| 0.05 mg/L 2,4-D | 16.67 bc | 1.00 b |
| Basic Media | 76.67 a | 1.56 ab |
| 300 mg/L timentin | 60.00 a | 1.33 ab |
| 0.1 mg/L TAA | 63.33 a | 2.08 ab |
| 0.1 mg/L IBA | 56.67 a | 2.30 a |
| 0.1 mg/L IAA | 76.67 a | 2.29 a |
| 0.1 mg/L NAA | 46.67 ab | 1.53 ab |
| 0.1 mg/L 2,4-D | 0.00 c | 0.00 c |

Fig. 3

| | TREATMENT (basic media + 1mg/L BAP + compound) | SHOOT REGENERATION (%) | MEAN NO. OF SHOOTS PER EXPLANT |
|---|---|---|---|
| Day 21 | 0.05 mg/L TAA | 36.67 ab | 1.17 a |
| | 0.05 mg/L NAA | 16.67 bc | 1.11 a |
| | 0.05 mg/L IAA | 40.00 ab | 1.75 a |
| | 0.05 mg/L IBA | 46.67 a | 1.25 a |
| | 0.05 mg/L 2,4-D | 0.00 c | 0.00 b |
| Day 28 | 0.05 mg/L TAA | 46.67 a | 1.17 ab |
| | 0.05 mg/L NAA | 26.67 ab | 1.23 ab |
| | 0.05 mg/L IAA | 56.67 a | 1.56 ab |
| | 0.05 mg/L IBA | 60.00 a | 1.58 a |
| | 0.05 mg/L 2,4-D | 0.00 b | 0.00 b |
| Day 21 | 0.1 mg/L TAA | 26.67 ab | 1.33 a |
| | 0.1 mg/L NAA | 0.00 b | 0.00 b |
| | 0.1 mg/L IAA | 23.33 ab | 1.67 a |
| | 0.1 mg/L IBA | 36.67 a | 1.69 a |
| | 0.1 mg/L 2,4-D | 0.00 b | 0.00 b |
| Day 28 | 0.1 mg/L TAA | 40.00 a | 1.31 a |
| | 0.1 mg/L NAA | 0.00 b | 0.00 b |
| | 0.1 mg/L IAA | 30.00 a | 1.61 a |
| | 0.1 mg/L IBA | 43.33 a | 1.56 a |
| | 0.1 mg/L 2,4-D | 0.00 b | 0.00 b |
| Day 21 | 0.5 mg/L TAA | 16.67 ab | 0.94 ab |
| | 0.5 mg/L NAA | 0.00 b | 0.00 b |
| | 0.5 mg/L IAA | 33.33 a | 1.00 ab |
| | 0.5 mg/L IBA | 23.33 ab | 1.08 a |
| | 0.5 mg/L 2,4-D | 0.00 b | 0.00 b |
| Day 28 | 0.5 mg/L TAA | 26.67 b | 1.53 a |
| | 0.5 mg/L NAA | 0.00 b | 0.00 b |
| | 0.5 mg/L IAA | 63.33 a | 1.42 a |
| | 0.5 mg/L IBA | 30.00 b | 1.18 a |
| | 0.5 mg/L 2,4-D | 0.00 b | 0.00 b |
| Day 21 | 1 mg/L TAA | 13.33 ab | 1.11 a |
| | 1 mg/L NAA | 0.00 b | 0.00 a |
| | 1 mg/L IAA | 20.00 a | 1.17 a |
| | 1 mg/L IBA | 0.00 b | 0.00 a |
| | 1 mg/L 2,4-D | 0.00 b | 0.00 a |
| Day 28 | 1 mg/L TAA | 26.670 ab | 2.5 a |
| | 1 mg/L NAA | 0.00 b | 0.00 b |
| | 1 mg/L IAA | 56.67 a | 1.18 ab |
| | 1 mg/L IBA | 6.67 b | 0.67 b |
| | 1 mg/L 2,4-D | 0.00 b | 0.00 b |
| Day 21 | 2 mg/L TAA | 33.3 a | 1.07 a |
| | 2 mg/L NAA | 6.70 b | 0.5 ab |
| | 2 mg/L IAA | 0.00 b | 0.00 b |
| | 2 mg/L IBA | 0.00 b | 0.00 b |
| | 2 mg/L 2,4-D | 0.00 b | 0.00 b |
| Day 28 | 2 mg/L TAA | 40.00 a | 1.28 a |
| | 2 mg/L NAA | 6.70 b | 0.5 ab |
| | 2 mg/L IAA | 16.7 ab | 1.44 a |
| | 2 mg/L IBA | 0.00 b | 0.00 b |
| | 2 mg/L 2,4-D | 0.00 b | 0.00 b |
| Day 21 | 10 mg/L TAA | 60.00 a | 7.33 a |
| | 50 mg/L TAA | 0.00 b | 0.00 b |
| | 100 mg/L TAA | 0.00 b | 0.00 b |
| | 200 mg/L TAA | 0.00 b | 0.00 b |
| | 300 mg/L TAA | 0.00 b | 0.00 b |
| Day 28 | 10 mg/L TAA | 76.66 a | 13.33 a |
| | 50 mg/L TAA | 0.67 b | 0.67 b |
| | 100 mg/L TAA | 0.00 b | 0.00 b |
| | 200 mg/L TAA | 0.00 b | 0.00 b |
| | 300 mg/L TAA | 0.00 b | 0.00 b |

Fig. 4

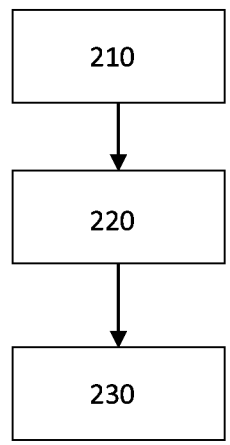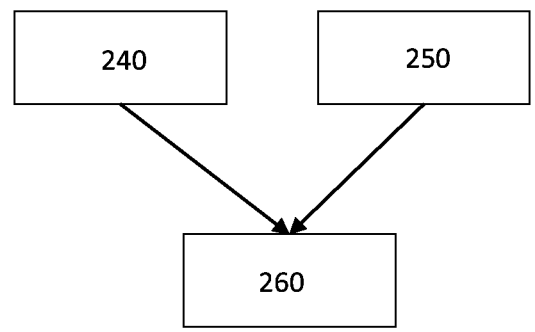
Fig. 5A             Fig. 5B

THIOPHENE ACETIC ACID FOR PLANT GROWTH REGULATION

TECHNICAL FIELD

The present disclosure concerns plant growth regulation. More particularly, but not exclusively, the present disclosure concerns thiophene acetic acid for plant growth regulation.

BACKGROUND OF THE INVENTION

Background description includes information that will be useful in understanding the present invention. It is not an admission that any of the information provided herein is prior art or relevant to the presently claimed invention, or that any publication specifically or implicitly referenced is prior art.

Plant growth regulators (PGRs) are natural or synthetic substances that help regulate plant growth and develop and include hormones and synthetic hormone analogues. PGR products are used in various industries such as agriculture, viticulture, and horticulture to improve plant growth and crop yield under non-ideal soil and environmental conditions. PGRs, especially auxins, and cytokinins are useful in vitro micro propagation of plants.

PGRs are commonly used in tissue culture to propagate multiple plants from a few explants. Similarly, they are used for the efficient regeneration of transgenic plants from explants after genetic transformation to develop modified plants with desirable traits. In the field, PGRs are often used to accelerate root and shoot growth and in turn, enhance yield. Plant hormones auxins and cytokinins are commonly used as PGRs.

To date, only a small number of auxins and cytokinins are commonly used in experiments involving in vitro regeneration. Examples of such auxins includes naturally occurring auxins indole-3-acetic acid (IAA), indole-3-butyric acid (IBA), 4-chloroindole-3-acetic acid (4-CI-IAA), and phenylacetic acid (PAA), and synthetic auxins naphthalene-1-acetic acid (NAA), 2,4-dichlorophenoxyacetic acid (2,4-D), and picloram, which are used in plant tissue culture.

However, a good regeneration protocol that works for one genotype would often require considerable modifications, especially in the case of hormones and their combinations, for different genotypes of the same species.

There is a need to identify new PGRs in order to develop new hormonal combinations for the efficient regeneration of different genotypes and recalcitrant species in vitro and for enhancing the growth of different species in the field.

The present disclosure seeks to mitigate at least one of the abovementioned problems. More particularly, but not exclusively, the present disclosure seeks to provide a new PGR.

SUMMARY

According to a first aspect of the present disclosure, there is provided a plant growth regulator comprising thiophene acetic acid.

The inventors discovered that shoot regeneration from tomato cotyledon explants in vitro was enhanced in the presence of the antibiotic timentin. They later discovered that timentin degrades into thiophene acetic acid (TAA) over time. They have surprisingly found that thiophene acetic acid (TAA) performs particularly well as a plant growth regulator. TAA was surprisingly found to enhance root and shoot formation and growth in explants, and in particular in cotyledon explants. TAA is also advantageous in that it may be used to enhance growth in whole plants.

In embodiments of the present disclosure, TAA may be beneficial in regulating growth of plants by inhibiting growth. The plant growth regulator may be a plant growth-inhibitor.

The thiophene acetic acid may be thiophene-3-acetic acid. The thiophene acetic acid may be thriophene-2-acetic acid. The thiophene acetic acid may be a combination of both thiophene-2-aceitc acid and thiophene-3-acetic acid.

The plant growth regulator may be suitable for plants with an auxin response pathway. The plant growth regulator may be suitable for tomato plants.

The plant growth regulator may be a plant growth-promoter.

The plant growth regulator may comprise 6-benzylaminopurine (BAP). The plant growth regulator may comprise cytokinins. The plant growth regulator may comprise kinetin. The plant growth regulator may comprise zeatin.

The addition of BAP has been found to have a synergistic effect with TAA. For example, shoot regeneration when enhanced with a combination of TAA and BAP may exceed other know auxins.

The concentration of 6-benzylaminopurine (BAP) may be between 0.5 mg/L and 2.0 mg/L. The concentration of BAP may be between 0.75 mg/L and 1.25 mg/L. The concentration of BAP may be substantially 1 mg/L. Substantially 1 mg/L corresponds to greater or equal to 0.95 mg/L and less than 1.05 mg/L.

The concentration of thiophene acetic acid may be greater than 0.05 mg/L. It has been found by the inventors that TAA is effective as a plant growth regulator even at relatively low concentrations.

The concentration of thiophene acetic acid may be between 0.05 mg/L and 50 mg/L. The concentration of thiophene acetic acid may be between 0.5 mg/L and 25 mg/L. The concentration of thiophene acetic acid may be between 1 mg/L and 15 mg/L. The inventors found that at this concentration range, the TAA outperformed other known auxins under the same conditions.

The concentration of thiophene acetic acid may be between 8 mg/L and 12 mg/L. At this concentration range other known auxins cease to be effective at shoot regeneration for example, while TAA approaches a very high effectiveness in shoot regeneration for example.

The plant growth regulator may comprise BAP.

The concentration of the BAP may be between 0.5 mg/L and 2 mg/L.

The inclusion of BAP has been found to enhance the effectiveness of the plant growth attributes of the TAA.

According to a second aspect of the present disclosure, there is provided a method of regulating growth of plants, the method comprising preparing a plant growth regulator comprising thiophene acetic acid according to the first aspect; and applying the plant growth regulator.

The plants may be plants with an auxin response pathway. The plants may be tomato plants.

The plants may be explants. The preparing may comprise supplementing a culture media with the plant growth regulator. The applying may comprise introducing the explants to the culture media.

The method may be performed in vitro.

In embodiments of the present disclosure, the plant growth regulator is supplemented to the culture media. In embodiments of the present disclosure, the explant is situated on the culture media such that it is allowed to develop.

It has been found that TAA is beneficial for regeneration, and as such it may be beneficial for example, for the regeneration of transgenic plants from explants after transformation. This is an important step in developing genetically modified plants with desirable traits.

The culture media may comprise Murashige and Skoog (MS) medium. The culture media may comprise sucrose gelled with agar.

The preparing may comprise forming a solution comprising the plant growth regulator such that the concentration of thiophene acetic acid is greater than 0.05 mg/L. The applying may comprise applying the solution comprising the plant growth regulator to the plants.

TAA may also, for example, provide beneficial plant growth regulation properties when applied to plants in the field. The plants in the field may be whole plants.

The applying may comprise watering the plants with the solution as a foliar spray.

According to a third aspect of the present disclosure, there is provided a fertiliser for regulating plant growth comprising a plant growth regulator according to the first aspect.

It will be appreciated that features disclosed in relation to one aspect of the present disclosure may be used in combination with another aspect of the present disclosure, and vice versa.

BRIEF DESCRIPTION OF THE DRAWINGS

The manner in which the above-recited features of the present invention is understood in detail, a more particular description of the invention, briefly summarized above, may be had by reference to embodiments, some of which are illustrated in the appended drawings. It is to be noted, however, that the appended drawings illustrate only typical embodiments of the present disclosure and are therefore not to be considered limiting of its scope, for the present disclosure may admit to other equally effective embodiments.

FIG. 3 shows a table of results of an experiment according to an embodiment of the present disclosure;

FIG. 4 shows a table of results of an experiment according to an embodiment of the present disclosure;

FIG. 5A shows a method of regulating plant growth according to an embodiment of the present disclosure;

FIG. 5B shows a method of regulating plant growth according to an embodiment of the present disclosure;

The foregoing and other objects, features and advantages of the present invention, as well as the invention itself, will be more fully understood from the following description of preferred embodiments, when read together with the accompanying drawings.

DETAILED DESCRIPTION OF THE DRAWINGS

The present disclosure relates to the field of plant growth regulation, and more particularly to the use of thiophene acetic acid for plant growth regulation.

The principles of the present invention and their advantages are best understood by referring to FIG. 1 to FIG. 7. In the following detailed description of illustrative or exemplary embodiments of the disclosure, specific embodiments in which the disclosure may be practiced are described in sufficient detail to enable those skilled in the art to practice the disclosed embodiments. The following detailed description is, therefore, not to be taken in a limiting sense, and the scope of the present disclosure is defined by the appended claims and equivalents thereof. References within the specification to "one embodiment," "an embodiment," "embodiments," or "one or more embodiments" are intended to indicate that a particular feature, structure, or characteristic described in connection with the embodiment is included in at least one embodiment of the present disclosure.

Figure 1:
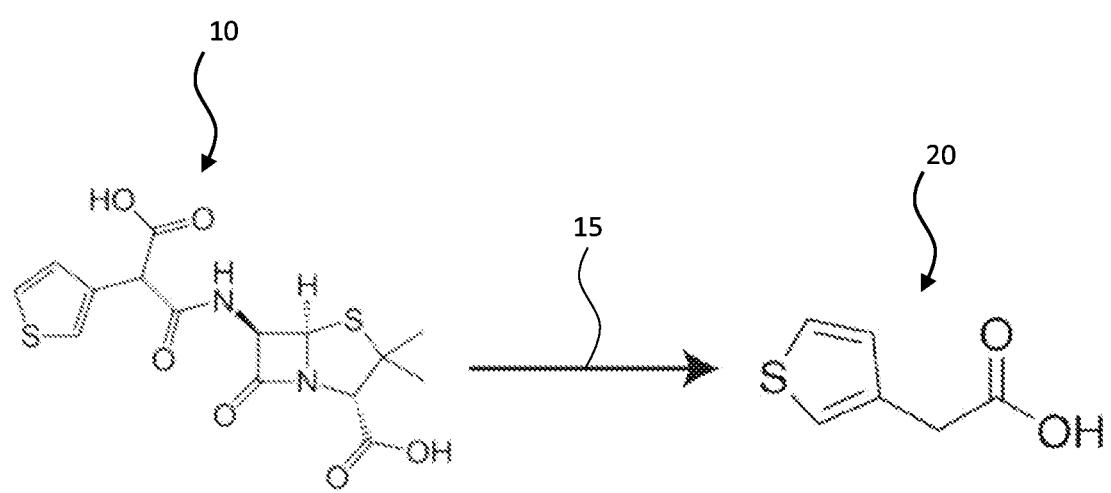
FIG. 1 shows a method of obtaining thiophene acetic acid according to an embodiment of the present disclosure.

FIG. 1 shows a method of obtaining thiophene acetic acid according to an embodiment of the present disclosure.

Ticarcillin 10 is the main component of the antibiotic timentin. Ticarcillin 10 degrades 15 naturally over time into thiophene acetic acid (TAA) 20. Thiophene acetic acid is characterised by the thiophene ring, connected to which, is an acetic acid group. The acetic acid group is connected to the thiophene ring in the 3 position i.e. the embodiment of FIG. 1 shows thiophene-3-acetic acid 20.

In embodiments of the present disclosure, the ticarcillin degrades into thiophene-2-acetic acid. In embodiments of the present disclosure, the ticarcillin degrades into both thiophene-2-acetic acid and thiophene-3-acetic acid.

A plant growth regulator of embodiments of the present disclosure comprises TAA. In embodiments, the plant growth regulator comprises a single isomer of TAA. In embodiments, the plant growth regulator comprises thiophene-2-acetic acid. In embodiments, the plant growth regulator comprises thiophene-3-acetic acid. In embodiments, the plant growth regulator comprises both thiophene-2-acetic acid and thiophene-3-acetic acid.

Figure 2:
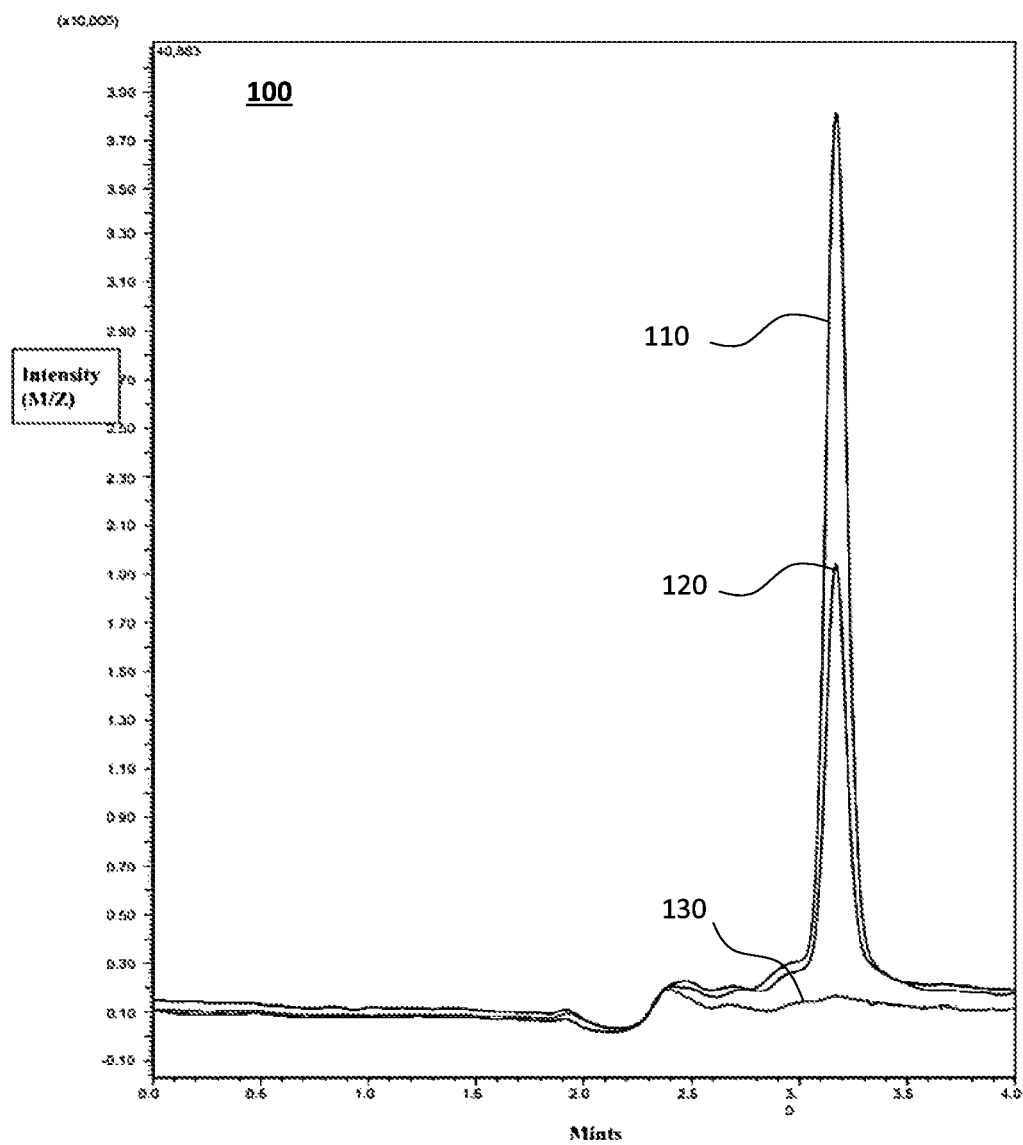
FIG. 2 shows a chart showing the degradation of ticarcillin into TAA according to an embodiment of the present disclosure.

FIG. 2 shows a chart 100 showing the degradation of ticarcillin into TAA according to an embodiment of the present disclosure. The chart 100 depicts the results of the following experiment 1:

Plant Material and Growth Conditions (Common to all Experiments)

Seeds of tomato cultivar Roma VF were sterilized by treating with 75% ethanol for 30 seconds at room temperature and washed with sterile water for five times. The seeds were then treated with 15% sodium hypochlorite for 10 minutes and washed five times in sterile water. The sterilized seeds were germinated on half-strength Murashige and Skoog (MS) medium in vitro. Cotyledons from 10-day old seedlings before first true leaves emerged were used as starting explants in all the experiments. The base and tip of the cotyledons were excised and the explants were transferred with the abaxial surface in contact with the culture medium. The basic culture medium consists of MS medium with vitamins supplemented with 30 g/L sucrose and gelled with 0.8% agar, and the pH of the medium was adjusted to 5.8±0.2. Plates were maintained at a light cycle of 16/8 hours day/night, temperature of 26/24° C. day/night, and relative humidity of 70% and subcultured on the same media after 14 days. Observations were made on 7, 14, 21 and 28 days of growth. All experiments were conducted with at least three replicates of 10 explants each.

Experiment 1

The Liquid Chromatography with tandem mass spectrometry (LC-MS/MS) analysis was carried out using a tandem mass spectrometer connected in tandem to an ultra-high-pressure liquid chromatography (UHPLC) system, consisting of a binary pump, auto-sampler, column compartment, DAD detector and degasser. The mass spectrometer was operated in both positive and negative electrospray ionization (ESI) modes. Nitrogen was used as heating and drying gases for samples.

The following samples were analysed for the presence of TAA; timentin 300 mg/L solution in sterile deionized water (0 and 28 day old), tomato cotyledon grown in the presence and absence of 300 mg/L timentin in basic culture media (0, 14 and 28 day old). The timentin solution in sterile deionized water was diluted further to prepare timentin 1 mg/L working solution and 10 μL was injected. The plant samples were powdered in liquid nitrogen and 0.5 g of the sample was weighed and mixed with 0.5 mL of deionized water. The sample was vortexed for 5 mins. This was followed by the addition of a solution of 5.0 mL of 1% formic acid in methanol, vortexed mixed, and centrifuged for 5 mins at 2000×g (4° C.). After that, the supernatant was filtered with a disposable membrane filter of 0.45 μm in pore size. Finally, 10 μL of the filtrate was injected into the LC-MS/MS system for analysis.

The LC-MS/MS analysis revealed that TAA was not present in the freshly prepared solution of 300 μg/mL timentin in water. However, after 14 and 28 days, TAA was detected in the samples, indicating that ticarcillin had degraded into TAA during that time. In plant samples grown without timentin, no TAA was detected in samples that were 0, 14, or 28 days old. On the other hand, in samples grown with timentin, 4.6 μg/mL TAA was detected in 14-day-old samples and 2.1 μg/mL was detected in 28-day-old samples. These findings confirm that ticarcillin degrades into TAA over time, which explains its presence in the plant samples (FIG. 2).

The results of FIG. 2 depict the results of this analysis. The line 130 shows the mass spectrometry chromatogram at 0 days, indicating that there is no TAA present in the freshly prepared solution. The line 110 is the peak at 14 days, and the line 120 is the peak at 28 days. This demonstrates that ticarcillin, the main component of timentin, degrades into TAA over time.

FIG. 3 shows a table of results of an experiment according to an embodiment of the present disclosure. The table of FIG. 3 corresponds to the results of Experiment 2, which is as follows:

Analysis of Effect of TAA and Commonly Used Auxins on Root Regeneration

In order to analyze the effect of TAA on root regeneration, the basic media were supplemented with different concentrations of TAA (0.05 and 0.1 mg/L) and further compared with individual effect of widely used auxins (IAA, NAA, IBA, 2,4 D) at similar concentrations.

Results of Experiment 2

The individual effects of TAA and commonly used auxins, IAA, NAA, IBA and 2,4D at two different concentrations (0.05 and 0.1 mg/L) on organogenesis from tomato cotyledon explants in basic culture media in the absence of any other hormones was analysed. Except 2,4 D, all the other hormones showed rapid root formation at both the concentrations within 7 days. Under both 2,4D concentrations, the explants enlarged in size and started showing signs of callus formation. Few explants showed tiny roots. By Day 14, explants on 2,4D containing media formed more callus and few of the explants showed longer roots.

The explants on other compounds containing media showed rapid root growth after Day 7. FIG. 3 shows that TAA performs on par with most known auxins for root regeneration, and is at least a viable alternative to known auxins.

FIG. 4 shows a table of results of an experiment according to an embodiment of the present disclosure. The table of FIG. 4 corresponds to the results of Experiment 3, which is as follows:

Analysis of Effect of TAA and Commonly Used Auxins on Shoot Regeneration

To analyse the effects on shoot regeneration, the basic media was supplemented with 1 mg/L BAP and different concentrations of TAA, IAA, NAA, IBA and 2,4 D (0.05, 0.1, 0.5, 1.0 and 2.0 mg/L) individually. Since there are no previous reports on suitable concentration ranges for TAA in tomato regeneration, concentrations at 50.0, 100.0, 200.0 and 300.0 mg/L were analysed additionally for TAA.

Results of Experiment 3

To analyse the effect of TAA and different auxins on shoot organogenesis, different concentrations of TAA, IAA, NAA, IBA and 2,4D (0.05, 0.1, 0.5, 1.0 and 2.0 mg/L) along with 1 mg/L BAP were analysed. In addition, the effect of higher concentrations of TAA (10.0, 50.0, 100.0, 200.0 and 300.0 mg/L) on shoot organogenesis was analysed. Shoot growth was observed only at low concentration of NAA (0.05 mg/L). At this concentration, most explants produced callus, but a few produced shoots. Higher concentrations of NAA produced mostly callus by Day 28, but a few of them showed root formation. IAA showed better shoot formation than NAA at 0.05, 0.1, 0.5 and 1.0 mg/L in combination with 1 mg/L BAP. The shoots at Day 28 were large and well defined. As the concentration of IAA increased, the number of explants with callus formation increased and at 2 mg/L, the plates showed mostly callus and root formation. Similar to IAA, IBA showed callus and well-defined shoot formation at lower concentrations (0.05, 0.1 and 0.5 mg/L) when used in combination with 1 mg/L BAP and at higher concentrations (1.0 and 2.0 mg/L), showed mostly callus and some root formation. 2,4D did not show any shoot formation at any of the concentrations (0.05, 0.1, 0.5, 1.0 and 2.0 mg/L) when used in combination with 1 mg/L BAP. The explants produced calluses at all concentrations. Lower concentrations of TAA (0.05, 0.1, 0.5, 1.0, 2.0 and 10.0 mg/L) started showing shoot formation around day 14 and many explants had well defined shoots by Day 28.

TAA at 10.0 mg/L showed the maximum number of shoots, and in fact, TAA at 10.0 mg/L showed greater shoot regeneration than any other tested auxin at any other concentration. Higher concentrations of TAA (50.0, 100.0 and 200.0 mg/L) did not show any shoot or root formation, instead showed callus formation. At 300 mg/L TAA, the explants showed necrosis within 7 days and by Day 28, all explants were dead.

The results shown in FIG. 4 demonstrate that TAA is a viable auxin analogue and facilitates the possibility of new combinations in new concentration regimes.

FIG. 5A shows a method of regulating plant growth according to an embodiment of the present disclosure.

Step 210 refers to a step of cultivating an explant. The step of cultivating comprises selecting seeds of the selected plant. The seeds are then treated and washed. The seeds are then germinated on a medium in vitro. Cotyledons from 10-day old seedlings before first true leaves emerge are used as starting explants.

In embodiments of the present disclosure, the treating of the seeds involves sterilisation in 75% ethanol. In embodiments of the present disclosure, the treating of the seeds comprises treatment with 15% sodium hypochlorite.

Step 220 refers to the step of preparing the culture media. The preparation of the culture media starts with preparing half-strength Murashige and Skoog (MS) medium. The germination medium is also supplemented with vitamins, supplemented with 30 g/L sucrose, and gelled with 0.8% agar.

Step 230 refers to the step of placing the explant in the culture media. Placing the explant in the culture media may also be known as introducing the explant to the culture media.

Step 230 comprises excising the base and tip of the cotyledons. The explants are transferred with the abaxial surface in contact with the culture medium.

FIG. 5B shows a method of regulating plant growth according to an embodiment of the present disclosure.

Where the method of FIG. 5A related to treatment of explants, the method of FIG. 5B relates to the treatment of whole plants, according to an embodiment of the present disclosure.

The treatment of whole plants may be approached from one of two routes. The first is the preparation of a liquid solution that is then used to treat and nourish the plant. The second is the preparation of a fortified compost that is used to grow the plant.

Step 240 relates to the step for preparation of solution of plant growth regulator comprising TAA. TAA and other vitamins, nutrients, auxins, and plant hormones selected for the desired plant growth regime is diluted in water to the desired concentrations to obtain the solution. The plant growth regulator solution applied to the whole plants in the field in step 260. The means of application can range from industrial machinery, to sprinklers, to sprays, to watering cans, for example. The application may be a spray onto the leaves of the plant, for example. In another use, the seedlings or cuttings may be treated with a liquid solution of plant growth regulator comprising TAA before being planted in the soil to enhance rooting, for example.

Step 250 relates to the step for preparation of compost comprising plant growth regulator comprising TAA. TAA and other vitamins, nutrients, auxins, and plant hormones selected for the desired plant growth regimes are mixed into the compost at the desired concentration. The compost is applied to whole plants in the field in step 260. The application of the compost, in embodiments, comprises sprinkling the compost onto the topsoil of the field. In embodiments of the present disclosure, the application of the compost comprises mixing the compost with the topsoil of the field.

Both steps 240 and 250 may more generally be termed as preparing the plant growth regulator.

Figure 6:
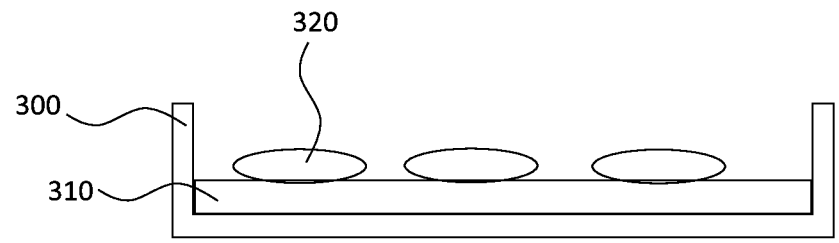
FIG. 6 shows a plant growth regulator according to an embodiment of the present disclosure.

FIG. 6 shows a plant growth regulator 310 according to an embodiment of the present disclosure. The plant growth regulator 310 comprises culture media and thiophene acetic acid. The plant growth regulator 310 is positioned in a petri dish 300 such that it is suitable for cultivating explants 320 in a controlled environment.

In embodiments of the present disclosure, the explants 320 originate from tomato plants/seeds, tobacco plants/seeds, and/or lettuce plants/seeds. Other explants belonging to plants that exhibit an auxin response pathway may be suitable, for example.

Figure 7:
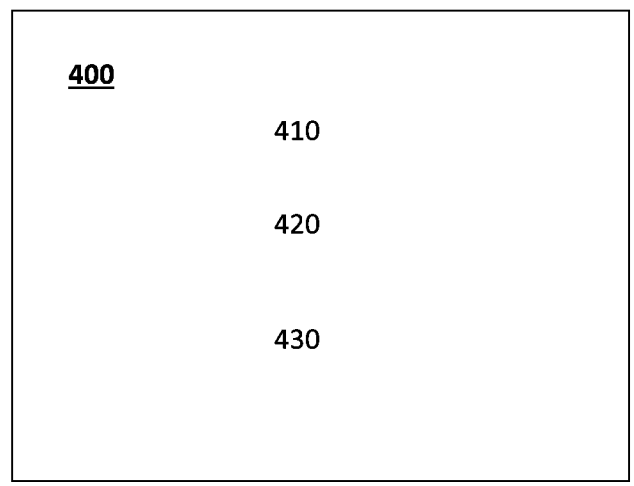
FIG. 7 shows a fertiliser according to an embodiment of the present disclosure.

FIG. 7 figuratively shows a fertiliser 400 according to an embodiment of the present disclosure.

The fertiliser 400 comprises TAA 410, compost 420, and other additives 430. The other additives 430 may comprise vitamins, minerals, nutrients, plant hormones, or auxins, for example. In embodiments of the present disclosure, the other additives 430 comprise BAP.

The fertiliser 400 would be applied to whole plants in the field either by application to the topsoil, or by mixing into the topsoil and/or the soil beneath.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents. The disclosures and the description herein are intended to be illustrative and are not in any sense limiting the present disclosure, defined in scope by the following claims.

Many changes, modifications, variations and other uses and applications of the present disclosure will become apparent to those skilled in the art after considering this specification and the accompanying drawings, which disclose the preferred embodiments thereof. All such changes, modifications, variations and other uses and applications, which do not depart from the spirit and scope of the present disclosure, are deemed to be covered by the invention, which is to be limited only by the claims which follow.

The invention claimed is:

1. A method of regenerating shoots of tomato explants with an auxin response pathway, the method comprising:
   preparing a plant growth regulator composition comprising 8 to 12 mg/L of thiophene acetic acid, 0.5 to 2 mg/L of 6-benzylaminopurine, and a culture media comprising Murashige and Skoog medium, sucrose, and gelled with agar; and
   applying the plant growth regulator composition to the tomato explants in vitro.

2. The method according to claim 1, wherein the applying comprises placing the tomato explants in the culture media.